United States Patent [19]

Schnettler et al.

[11] 4,418,071

[45] Nov. 29, 1983

[54] CARDIOTONIC IMIDAZOLECARBOXYLIC ACID DERIVATIVES

[75] Inventors: Richard A. Schnettler; Richard C. Dage, both of Cincinnati, Ohio; J. Martin Grisar, Strasbourg, France

[73] Assignee: Merrell Dow Pharmaceuticals Inc., Cincinnati, Ohio

[21] Appl. No.: 317,956

[22] Filed: Nov. 4, 1981

[51] Int. Cl.³ .......................................... A61K 31/415
[52] U.S. Cl. ................................. 424/273 R; 548/321
[58] Field of Search ................................... 424/273 R

[56] References Cited

FOREIGN PATENT DOCUMENTS 2009741 6/1979 United Kingdom.

OTHER PUBLICATIONS

*Chemical Abstracts*, 87:152201a (1977) [Miyoshi et al., Japan Kokai No. 77 46,074, 4/12/77].
*Chemical Abstracts*, 87:5972z (1977) [White, Ger. Offen. No. 2,634,430, 2/10/77].

*Primary Examiner*—Richard A. Schwartz

*Attorney, Agent, or Firm*—Stephen L. Nesbitt; Raymond A. McDonald; Gary D. Street

[57] ABSTRACT

The use of novel imidazolecarboxylic acid derivatives of the following general structure which are useful as antihypertensives, cardiotonics and antithrombotics

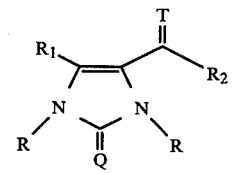

wherein Q and T are an oxygen or sulfur atom; R is hydrogen, lower alkyl, lower alkylcarbonyl or benzoyl; $R_1$ is hydrogen or $-CH(R_3)R_4$; $R_2$ is lower alkoxy, phenoxy or phenoxy substituted at the ortho, meta, or para position with lower alkyl, lower alkoxy, hydroxy, halogen, trifluoromethyl, lower alkylthio, lower alkylsulfone, or lower alkylsulfoxide; $R_3$ is hydrogen or lower alkyl; $R_4$ is hydrogen, hydroxy, lower alkoxy, lower alkylcarbonyl, $-ONO_2$ or halogen; and their pharmaceutically acceptable salts thereof.

5 Claims, No Drawings

CARDIOTONIC IMIDAZOLECARBOXYLIC ACID DERIVATIVES

FIELD OF THE INVENTION

This invention relates to the use of imidazolecarboxylic acid derivatives as antihypertensives, cardiotonics and antithrombotics.

SUMMARY OF THE INVENTION

This invention is directed to the use of imidazolecarboxylic acid derivatives of the general Formula I

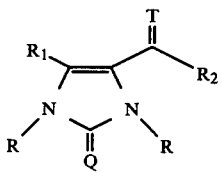

Formula 1 wherein Q and T are each independently an oxygen atom or a divalent sulfur atom; R is hydrogen, lower alkyl, lower alkylcarbonyl or benzoyl; $R_1$ is hydrogen or $-CH(R_3)R_4$; $R_2$ is lower alkoxy, phenoxy or phenoxy substituted at the ortho, meta or para position with lower alkyl, lower alkoxy, hydroxy, halogen, trifluoromethyl, lower alkylthio, lower alkylsulfone, or lower alkylsulfoxide; $R_3$ is hydrogen or lower alkyl; $R_4$ is hydrogen, hydroxy, lower alkoxy, lower alkylcarbonyloxy, $-ONO_2$ or halogen; and their pharmaceutically acceptable salts thereof as antihypertensives, cardiotonics and antithrombotics.

DESCRIPTION OF THE PREFERRED EMBODIMENTS

As used herein, the term "lower alkyl" includes straight and branched chain alkyl of from 1 to 4 carbon atoms such as methyl, ethyl, isopropyl, n-butyl and isobutyl.

As used herein, the term "lower alkylcarbonyl" is taken to mean a group of the structure

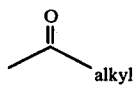

wherein the alkyl moiety is a straight or branched alkyl of from 1 to 4 carbon atoms such as methyl, ethyl, isopropyl, n-butyl and isobutyl.

As used herein, the term "benzoyl" is taken to mean a group of the formula $-(CO)C_6H_5$.

As used herein, the term "lower alkoxy" includes straight and branched chain alkoxy of from 1 to 4 carbon atoms such as methoxy, ethoxy, isopropoxy, n-butoxy and isobutoxy.

As used herein, the term "lower alkylcarbonyloxy" is taken to mean a group of the structure

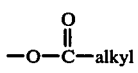

wherein the alkyl moiety is a straight or branched chain alkyl of from 1 to 4 carbon atoms such as methyl, ethyl, isopropyl, n-butyl and isobutyl.

As used herein, the term "halogen" includes fluorine, chlorine, bromine or iodine.

As used herein, the term "halide" includes fluoride, chloride, bromide, or iodide.

As used herein, the term "lower alkylthio" includes straight and branched chain alkylthio of from 1 to 4 carbon atoms such as methylthio, ethylthio, isopropylthio, n-butylthio and isobutylthio.

As used herein, the term "lower alkylsulfone" is taken to mean a group of the structure

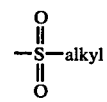

wherein the alkyl moiety is a straight or branched alkyl of from 1 to 4 carbon atoms such as methyl, ethyl, isopropyl, n-butyl or isobutyl.

As used herein, the term "lower alkylsulfoxide" is taken to mean a group of the structure

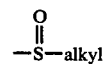

wherein the alkyl moiety is a straight or branched alkyl of from 1 to 4 carbon atoms such as methyl, ethyl, isopropyl, n-butyl or isobutyl.

The preferred compounds of this invention are those compounds of Formula 1 wherein Q and T are each oxygen atoms.

The more preferred compounds of this invention are those compounds of Formula 1 wherein R is hydrogen. Also included among those compounds of this invention considered more preferred are those compounds of Formula 1 wherein $R_4$ is lower alkoxy or lower alkylcarbonyloxy.

The most preferred compounds of this invention are those compounds of Formula 1 wherein $R_2$ is methoxy, ethoxy or phenoxy. Also included among those compounds of this invention considered most preferred are those compounds of Formula 1 wherein $R_4$ is hydrogen, methyl, hydroxy, methoxy, ethoxy or acetyloxy.

As examples of compounds of Formula 1 there may be mentioned the following:

Methyl 2-oxo-imidazole-4-carboxylate;

Phenyl 5-methyl-2-thioxo-imidazole-4-carboxylate;

(3-methylphenyl) 5-(bromomethyl)-2-oxo-imidazole-4-carboxylate;

(2-hydroxyphenyl) 5-(1-ethoxyethyl)-2-oxo-imidazole-4-carboxylate;

(4-methylthiophenyl) 5-ethyl-2-oxo-imidazole-4-carboxylate;

ethyl 5-acetoxymethyl-2-oxo-imidazole-4-carboxylate;

(3-chlorophenyl) 5-hydroxymethyl-2-oxo-imidazole-4-carboxylate nitrate ester;

(4-t-butylphenyl) 5-(1-hydroxyethyl)-2-oxo-imidazole-4-thiocarboxylate;

Propyl 1,3-diacetyl-5-isobutyl-2-oxo-imidazole-4-carboxylate;

Phenyl 1,3-isopropyl-5-acetoxymethyl-2-oxo-imidazole-4-carboxylate.

Those compounds of Formula 1 wherein R is hydrogen are acidic and may form pharmaceutically active salts of Formula 2

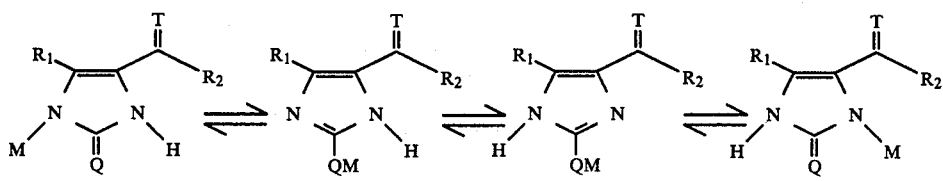

Formula 2 wherein Q, T, $R_1$ and $R_2$ are as defined in Formula 1, and M is a pharmaceutically acceptable alkali metal such as sodium or potassium; alkaline earth metal such as calcium or magnesium; transition metal such as zinc or iron; or main group metal.

In general, the compounds of this invention are prepared by standard techniques analogously known in the art.

More specifically, the imidazolecarboxylic acid derivatives of the invention wherein T is an oxygen atom and R is hydrogen are well known in the prior art and may be prepared by reaction of an aminoketocarboxylate of Formula 3

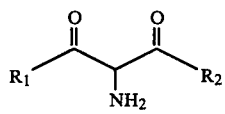

Formula 3 wherein $R_1$ and $R_2$ are as defined in Formula 1 with a cyanate or thiocyanate salt, as appropriate, preferably a sodium or potassium cyanate or thiocyanate. This reaction is performed by mixing about 1 molar equivalent of the appropriate aminoketocarboxylate with about 1 to about 5 molar equivalents, preferably about 1 molar equivalent, of a cyanate or thiocyanate salt in a suitable solvent. The reaction is allowed to proceed for about 5 minutes to about 10 hours depending on the reactants, the solvent and the temperature which can be from about $-10°$ to about $50°$ C., preferably $0°$ C. Suitable solvents for this reaction are any non-reactive solvent, preferably water miscible solvent, for example, an organic acid such as acetic acid; an alcohol such as methanol or ethanol; or an ether such as tetrahydrofuran or p-dioxan. Preferably the solvent is mixed with water. The preferred solvent is aqueous ethanol.

The product of this reaction may be isolated by any art-known procedure such as by conversion to the corresponding sodium or potassium salt and reprecipitation with carbon dioxide or a mineral acid such as dilute hydrochloric acid.

When it is desired that T be a divalent sulfur atom, the corresponding imidazolecarboxylic acid of Formula 1 wherein T is an oxygen atom is reacted with phosphorus pentasulfide, $P_2S_5$, by procedures generally known in the art. This reaction may be performed by mixing about 1 molar equivalent of the imidazolecarboxylic acid wherein T is an oxygen atom, with about 1 to about 5 molar equivalents, preferably about 1 molar equivalent, of $P_2S_5$, together with a suitable solvent. This reaction is allowed to proceed for about 1 to about 10 hours, preferably about 5 hours, depending on the reactant, the solvent and the temperature which can be from about $25°$ C. to about $125°$ C., preferably about $80°$ C. A suitable solvent for this reaction is any non-reactive solvent, for example, tetrahydrofuran, p-dioxan, benzene, toluene or pyridine. The preferred solvent is pyridine.

When desired, one or both of the nitrogen atoms of the imidazole ring may be substituted with an alkyl group by any art-known procedure. Such methods include reacting the appropriate N-unsubstituted imidazolecarboxylic ester of this invention with a base and an alkylating agent in the presence of an unreactive solvent. Suitable bases for this reaction can be, for example, a hydride such as sodium hydride or calcium hydride; or an alkoxide such as sodium ethoxide. Suitable alkylating agents for this reaction are, for example, an alkyl halide such as methyl iodide; or a dialkylsulfate such as dimethylsulfate. Suitable unreactive solvents are, for example, dimethylformamide (DMF) or dimethylsulfoxide (DMSO). The reaction is allowed to proceed from about 1 hour to about 10 hours and the temperature may be from about $0°$ to about $100°$ C., preferably about $25°$ C. When it is desired that only one of the imidazole ring nitrogen atoms be substituted with an alkyl group, the appropriate imidazolecarboxylic ester is reacted with from about 1 molar equivalent of an alkylating agent. Utilizing this procedure, both possible monoalkylated nitrogen isomers result. These isomers are separable by conventional art-known procedures such as fractional crystallization, fractional distillation or chromatography. When it is desired that both nitrogen atoms of the imidazole ring be alkyl substituted, the appropriate imidazolecarboxylic ester is reacted with from about 2 molar equivalents to about 10 molar equivalents of a base, preferably about 2 molar equivalents and from about 2 molar equivalent to about 10 molar equivalents of an alkylating agent, preferably about 2 molar equivalents. Finally, any hydroxy substituents, if present, may become alkylated concurrently. That is, when $R_4$ is hydroxy or when $R_2$ is a phenoxy substituted with hydroxy, such groups are alkylated under identical reaction conditions. If desired, the alkylation of these substituents may be avoided by the use of suitable protecting groups well-known in the art, for example, hydroxy groups may be benzylated and later deblocked by hydrogenolysis.

When desired, the nitrogen atoms of the imidazole ring may be substituted with an alkylcarbonyl or benzoyl group by any suitable art-known procedure. Such methods include reacting the ring N-unsubstituted imidazolecarboxylic ester of this invention with an acid anhydride. The reactions are allowed to proceed for about 1 hour to about 20 hours, preferably about 5 hours and the temperature may be from about $0°$ to about $200°$ C. preferably $135°$ C. Finally, any hydroxy substituents, if present, will become acylated or benzoylated concurrently. That is, when $R_4$ is hydroxy or when $R_2$ is a phenoxy substituted with hydroxy, such groups are acylated under identical reaction conditions. If desired, the acylation of these substituents may be avoided by the use of suitable protecting groups well-known in the art, for example hydroxy groups may be benzylated and later deblocked by hydrogenolysis.

The alkali metal, alkaline earth metal, transition metal or main group metal, salts of the imidazolecarboxylic esters of this invention may be prepared from a corresponding metal alkoxide, such as sodium methoxide or potassium ethoxide, or a metal hydride such as calcium hydride. Suitable solvents are, for example, lower alcohols, such as methanol, ethanol, isopropanol, n-propanol or n-butanol, dimethylformanide or dimethylsulfoxide. The imidazolecarboxylic acid derivative and base are allowed to react for about 1 minute to about 24 depending on the reactants and the temperature which can be from about $-78°$ to about $150°$ C., preferably from about $0°$ to about $25°$ C.

The aminoketocarboxylate of Formula 3 may be prepared by reduction of the appropriate oxime of Formula 4

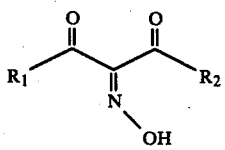

Formula 4 wherein $R_1$ and $R_2$ are as defined above in Formula 1. These oximes are reduced by any suitable method generally known in the art such as catalytically in acidic alcoholic medium such as ethanol hydrochloric acid over an appropriate noble metal catalyst such as palladium on charcoal or with zinc or tin in acetic acid/acetic anhydride solution.

The oximes of Formula 4 may be prepared by any suitable art-known procedure such as nitrosation of the appropriate $\beta$-ketoesters of Formula 5

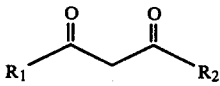

Formula 5 wherein $R_1$ and $R_2$ are as defined above in Formula 1. Suitable nitrosation reactions are reviewed by O. Tousler in "Organic Reactions," volume VII, pp. 327–377.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic. In many respects these compounds possess digitalis-like action. The compounds of general Formula 1 may also be used in the treatment of hypertension including primary or essential hypertension, hormonally induced hypertension, renal hypertension and chemically induced hypertension. Finally, the compounds of general Formula 1 may be used as antithrombotics. They affect the coagulation of blood by preventing the aggregation of blood platelets, which play a dominant role in thrombotic conditions both in the initial event and at the occlusive stage. Arterial thrombosis, particularly in arteries supplying the heart muscle and brain, is a leading cause of death and disability.

The utility of Formula 1 compounds as antihypertensives may be determined by administering the test compound (50 mg/5 kg p.o.) to six spontaneously hypertensive rats (having a systolic blood pressure greater than 150 mm Hg) at 50 mg/5 ml/kg using 0.5% methylcellulose. Caudal artery blood pressure is recorded via a photocell transducer placed over the tail just behind the pressure cuff. Three readings of approximately 2 minutes are made 1, 2, 3, 4 and 24 hours after dosing. A compound in this test is considered active if the mean fall in blood pressure is significantly ($p<0.05$) greater than control for at least one of the 1, 2, 3, 4, or 24 hours post-drug treatment time periods.

The utility of Formula 1 compounds as cardiotonics may be determined by administering the test compound (0.1–10 mg/kg) intravenously, intraperitoneally, intraduodenally or intragastrically in a suitable vehicle to a mongrel dog (either sex). The test dogs are anesthetized and prepared by isolating a suitable artery (e.g. femoral or common carotid) and vein (e.g., femoral or external jugular); introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to measure myocardial contractile force. An electromagnetic flow probe may be placed around the root of the ascending aorta for measuring cardiac output less coronary blood flow. The aorta and vena cava may be connected to measure the venous return to the heart. Alternatively the heart and the lungs may be vascularly isolated from the rest of the circulatory system. Heart failure is induced by administering sodium pentobarbital (20–40 mg/kg injection followed by a constant infusion of 0.25 mg/kg/min), by administering propranalol hydrochloride (4 mg/kg injection followed by a constant infusion of 0.18 mg/kg/min) intravenously, or by administering sodium pentobarbital (0.15 mg/ml) into the blood perfusing the heart. Following administration of any of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the severity of the cardiac failure and the mode of administration.

For oral or parenteral administration the cardiotonically effective amount of compound is from about 0.01 mg/kg of patient body weight per day up to about 500 mg/kg of patient body weight per day and preferably from about 0.1 mg/kg of patient body weight per day up to about 50.0 mg/kg of patient body weight per day.

For oral administration a unit dosage may contain, for example, from 1 to 500 mg of the active ingredient. For parenteral administration a unit dosage may contain, for example, from 1 to 50 mg of the active ingredient. Repetitive daily administration of the compounds may be desired and will vary with the condition of the patient and the mode of administration.

As used herein the term patients is taken to mean warm blooded animals, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The following are illustrative examples of the preparation and use of the compounds of this invention.

EXAMPLE 1

1,1-Dimethylethyl 2,3-Dihydro-5-methyl-2-oxo-1H-imidazole-4-carboxylate

To a solution of 31.6 g (0.2 ml) of tert-butyl acetoacetate in 30 ml of acetic acid, stirred and cooled in an ice-methanol bath, is added dropwise over 70 minutes a solution of 15.2 g (0.22 ml) of sodium nitrite in 50 ml of water. The mixture is stirred for 2 hours at 0° C., and 500 ml of ethyl ether is added. The ethereal solution is washed with water, sodium bicarbonate solution, sodium chloride solution, and is dried over magnesium sulfate. The solvent is evaporated leaving 36.4 g of an oil that is tert-butyl 2-(oximino)-3-oxobutanoate.

The oil is dissolved in 300 ml of ethanol and 200 ml of 2 N hydrochloric acid. 2.0 g of 10% palladium on charcoal is added and the mixture is shaken under hydrogen gas in a Parr shaker until 2 molar equivalents of hydrogen are consumed (about 2 hours). The catalyst is removed by filtration to given an acidic solution of tert-butyl 2-amino-3-oxo-butanoate, which is divided into 2 equal portions.

To one half of the above solution is added 16.2 g (0.2 ml) of potassium cyanate and the mixture is heated on a steam bath for 1 hour. The solution, which becomes neutral, is acidified with 2 N hydrochloric acid and the product crystallizes on cooling. Recrystallization from a mixture of ethanol and water gives the title compound, m.p. 225° C. (dec.).

EXAMPLE 2

Ethyl 2,3-Dihydro-5-methyl-2-oxo-1H-imidazole-4-carboxylate

This compound was prepared in the manner described in example 1, m.p. 217°–220° C. Synthesis of this compound was first described by Gabriel and Posner, Ber., 27, 1144 (1894).

EXAMPLE 3

Ethyl 5-Ethyl-2,3-dihydro-2-oxo-1H-imidazole-4-carboxylate

This compound was prepared in the manner described in example 1, m.p. 186°–189° C. Synthesis of this compound was first described by Duschinsky and Dolan, J. Am. Chem. Soc., 68, 2350 (1946).

EXAMPLE 4

Ethyl 1,3-Diacetyl-2,3-dihydro-5-methyl-2-oxo-1H-imidzole-4-carboxylate

A mixture of 54.5 g (0.32 ml) of ethyl 2,3-dihydro-5-methyl-2-oxo-1H-imidazole-4-carboxylate and 240 ml of acetic anhydride is stirred at reflux temperature for 13 hours. Acetic anhydride and the acetic acid that forms is distilled off (150 ml) and is replaced by fresh acetic anhydride. After another 9 hours of reflux the mixture is evaporated under reduced pressure and the oily residue is triturated with cyclohexane. The resulting crystalline material is dissolved in 600 ml of boiling cyclohexane, a small amount of insoluble material is removed by decantation, the solution is decolorized by treatment with charcoal (which is filtered off), 400 ml of hexane is added and the solution is allowed to cool ($-20°$ C.). The crystalline product is collected, 48.4 g (56%), m.p. 56°–58° C. (dec.).

EXAMPLE 5

Ethyl 1,3-Diacetyl-5-(bromomethyl)-2,3-dihydro-2-oxo-1H-imidazole-4-carboxylate

A mixture of 12.7 g (0.05 ml) of ethyl 1,3-diacetyl-2,3-dihydro-5-methyl-2-oxo-1H-imidazole-4-carboxylate (example 3), 9.3 g (0.052 ml) of N-bromosuccinimide and about 100 mg of benzoyl peroxide in 400 ml of carbon tetrachloride is refluxed for 4 hours with stirring. The mixture is cooled in ice, the precipitated succinimide is removed by filtration, and the filtrate is evaporated to give 28.8 g of an oil. An NMR spectrum (in CDCl$_3$) shows this to be the title compound.

EXAMPLE 6

Ethyl 3-acetyl-5-(bromomethyl)-2,3-dihydro-2-oxo-1H-imidazole-4-carboxylate

Crude ethyl 5-(bromomethyl)-1,3-diacetyl-2,3-dihydro-2-oxo-1H-imidazole-4-carboxylate is dissolved in 30% hydrobromic acid in acetic acid and the solution is allowed to stand at room temperature for 4 hours. The product precipitates, is collected and dried in vacuo at 80° C. over KOH, m.p. 193°–194° C. (dec.).

EXAMPLE 7

Ethyl 3-acetyl-5-[(acetyloxy)methyl]-2,3-dihydro-2-oxo-1H-imidazole-4-carboxylate To a solution of compound of Example 1 (2.9 g) 60 ml of acetic acid is added 1.7 g of silver acetate and the mixture is stirred at 25° C. for 6 hours. Silver salts are removed by filtration and the filtrate is evaporated to dryness. The residue is recrystallized twice from ethyl acetate/hexane (1:1) to give the title compound, m.p. 138°–139° C.

EXAMPLE 8

Ethyl 1,3-Diacetyl-2,3-dihydro-5-(hydroxmethyl)-2-oxo-1H-imidazole-4-carboxylate nitrate ester To a cold (0° C.) solution of 8.5 g (0.05 ml) of silver nitrate in 100 ml of dry acetonitrile is added dropwise over 30 minutes a solution of 8.3 g (approximately 0.025 ml) of crude ethyl 1,3-diacetyl-5-(bromomethyl)-2,3-dihydro-2-oxo-1H-imidazole-4-carboxylate (example 4) in 40 ml of acetonitrile. The mixture is stirred for 45 minutes at 0° C. The precipitated silver bromide is removed by filtration and the filtrate is evaporated to dryness. The residue is partitioned between ethyl acetate and water, the ethyl acetate solution is washed with water and dried over magnesium sulfate, and the solvent is evaporated. The resulting oil is crystallized from a mixture of ethyl acetate and hexane, and recrystallized from ethyl acetate to give the title compound, m.p. 84°–85° C.

EXAMPLE 9

Cardiotonic Activity of 5-Alkyl-2,3-dihydro-2-oxo-1H-imidazole-4-carboxylic Acid Esters Mongrel dogs of 1–3 kg body weight were anesthethized with 35 mg/kg iv of pentobarbital sodium. Their chests were opened surgically and a pericardial cradle was formed to support the heart. A Brodie-Walton strain gage was sutured to the left ventrical to monitor myocardial contractile force. Devices to monitor heart rate and arterial blood pressure were also attached.

Test compounds were weighted and dissolved in dimethylacetamide and diluted with water to known concentrations and the solutions were infused intravenously through polyethylene catheters filled with 0.1% Heparin sodium. The amount of test compound infused was adjusted to give 0.3, 1 and 3 mg per kg of body weight of the animal.

The increase of myrocardial contractile force following administration of test compound at each concentration was measured. From these measurements the effective dose, that is the dose that causes an increase of contractile force of 30% for a duration of at least 20 minutes, was calculated.

The following results were obtained:

| Compound | Effective Dose mg/kg/IV |
| --- | --- |
| 1 | 0.45 |
| 2 | 0.44 |
| 3 | 0.51 |

Compound 1: Ethyl 5-methyl-2-oxo-1H-imidazole-4-carboxylate
Compound 2: 1,1-Dimethylethyl 5-methyl-2-oxo-1H-imidazole-4-carboxylate
Compound 3: Ethyl 5-ethyl-2-oxo-1H-imidazole-4-carboxylate

We claim:

1. A method for the treatment of a condition requiring the strengthening of heart action in a patient in need thereof which comprises administering to said patient a cardiotonically effective amount of a compound of the formula

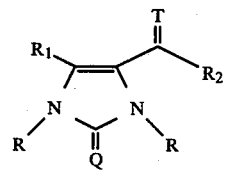

wherein Q and T are each independently an oxygen atom or a divalent sulfur atom; R is hydrogen, lower alkyl, lower alkylcarbonyl or benzoyl; $R_1$ is hydrogen, or $-CH(R_3)R_4$; $R_2$ is lower alkoxy, phenoxy or phenoxy substituted at the ortho, meta or para position with lower alkyl, lower alkoxy, hydroxy, halogen, trifluoromethyl, lower alkylthio, lower alkylsulfone or lower alkylsulfoxide; $R_3$ is hydrogen or lower alkyl; $R_4$ is hydrogen, hydroxy, lower alkoxy, lower alkylcarbonyloxy, $-ONO_2$, or halogen; or a pharmaceutically acceptable salt thereof.

2. A method of claim 1 wherein Q and T are each oxygen atoms.

3. A method of claim 2 wherein $R_1$ is methyl and $R_2$ is lower alkoxy.

4. A method of claim 2 wherein $R_1$ is ethyl and $R_2$ is lower alkoxy.

5. A method of claim 2 wherein R is hydrogen.

* * * * *